(12) United States Patent
Bauer et al.

(10) Patent No.: US 10,258,772 B2
(45) Date of Patent: Apr. 16, 2019

(54) SAFETY NEEDLE ARRANGEMENT FOR DRAWING FLUID FROM A BODY

(71) Applicant: Greiner Bio-One GmbH, Kremsmuenster (AT)

(72) Inventors: Christian Bauer, Kremsmuenster (AT); Franz Ebetsberger, Kremsmuenster (AT); Franz Kirchmeir, Leonding (AT); Andreas Mayr, Sierning (AT); Melanie Christina Schimpl, Linz (AT); Gerhard Strasser, Kremsmuenster (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 159 days.

(21) Appl. No.: 15/326,884

(22) PCT Filed: Jul. 16, 2015

(86) PCT No.: PCT/AT2015/050169
§ 371 (c)(1),
(2) Date: Jan. 17, 2017

(87) PCT Pub. No.: WO2016/007981
PCT Pub. Date: Jan. 21, 2016

(65) Prior Publication Data
US 2017/0203050 A1    Jul. 20, 2017

(30) Foreign Application Priority Data
Jul. 18, 2014  (AT) .............................. A 50500/2014

(51) Int. Cl.
*A61M 25/06*    (2006.01)
*A61M 5/32*    (2006.01)

(52) U.S. Cl.
CPC ...... *A61M 25/0631* (2013.01); *A61M 5/3257* (2013.01); *A61M 25/0637* (2013.01)

(58) Field of Classification Search
CPC ............ A61M 5/3257; A61M 25/0631; A61M 25/0637; A61M 25/0612; A61M 5/322; A61M 5/321
See application file for complete search history.

(56) References Cited

U.S. PATENT DOCUMENTS 5,779,679 A * 7/1998 Shaw ................ A61M 25/0637
604/158
5,928,199 A * 7/1999 Nakagami ............. A61M 5/158
604/171

(Continued)

FOREIGN PATENT DOCUMENTS

DE  10 2009 052 962 A1  6/2011
EP    0 830 871 B1    9/2003

(Continued)

OTHER PUBLICATIONS

International Search Report of PCT/AT2015/050169, dated Nov. 17, 2015.

(Continued)

*Primary Examiner* — Bhisma Mehta
*Assistant Examiner* — James D Ponton
(74) *Attorney, Agent, or Firm* — Collard & Roe, P.C.

(57) ABSTRACT

The invention relates to a safety needle arrangement (1) comprising a main part (2), a cannula support (6), a cannula (10), a proximal end of which is retained on a distal end (7) of the cannula support (6), an adjusting element (15) which is operatively arranged between the main part (2) and the cannula support (6), and a locking device (19) with multiple first and second locking elements (20, 21) which are engaged with one another. The first locking elements (20) are arranged in the region of a proximal end (4) of the main (Continued)

part (2) and are formed by projections (22) which are arranged diametrically opposite one another. The second locking elements (21) are arranged in the region of a proximal end (8) of the cannula support (6) and are formed by recesses (24) which are arranged diametrically opposite one another.

10 Claims, 4 Drawing Sheets

(56) References Cited

U.S. PATENT DOCUMENTS

| | | |
|---|---|---|
| 6,790,199 B1 | 9/2004 | Gianakos |
| 9,381,324 B2 | 7/2016 | Fuchs et al. |
| 2003/0078540 A1 | 4/2003 | Saulenas et al. |
| 2007/0016148 A1 | 1/2007 | Iwase et al. |
| 2008/0082054 A1* | 4/2008 | Iwase .................. A61M 5/158 604/198 |
| 2011/0071469 A1 | 3/2011 | Wilson et al. |

FOREIGN PATENT DOCUMENTS

| | | |
|---|---|---|
| WO | 02/26284 A2 | 4/2002 |
| WO | 2009/021263 A1 | 2/2009 |

OTHER PUBLICATIONS

Response dated Jun. 7, 2016 from the European patent attorney to the European Patent Office regarding PCT/AT2015/050169 with an English translation of the relevant parts.

\* cited by examiner

SAFETY NEEDLE ARRANGEMENT FOR DRAWING FLUID FROM A BODY

CROSS REFERENCE TO RELATED APPLICATIONS

This application is the National Stage of PCT/AT2015/050169 filed on Jul. 16, 2015, which claims priority under 35 U.S.C. § 119 of Austrian Application No. A 50500/2014 filed on Jul. 18, 2014, the disclosures of which are incorporated by reference. The international application under PCT article 21(2) was not published in English.

The invention relates to a safety needle arrangement and a method for drawing fluid from a body.

US 2007/0016148 A1 describes a safety needle arrangement of the generic type, comprising a main part having a distal end and a proximal end, and an end-to-end orifice extends through the main part between the distal end of the main part and the proximal end of the main part. The safety needle arrangement further comprises a cannula support having a distal end and a proximal end, and a flow orifice extends between the two ends of the cannula support. The cannula support is accommodated in the end-to-end orifice of the main part so as to be displaceable in the axial direction. A cannula has a distal end and a proximal end and a flow passage extends inside the cannula between the two ends of the latter, and the proximal end of the cannula is retained on the distal end of the cannula support. An adjusting element is operatively disposed between the main part and the cannula support, and the adjusting element and the cannula support together with the cannula retained on it can be automatically moved from a first position in which the cannula projects beyond the distal end of the main part into a second position in which at least the distal end of the cannula is covered by the main part. A locking device has several first and second locking elements. When the first and second locking elements are in a mutually engaged first position, the locking device locks the first position of the cannula support together with the cannula relative to the main part. The first locking elements are disposed in the region of the proximal end of the main part and the second locking elements are disposed in the region of the proximal end of the cannula support. The disadvantage of this is that when the locking device is unlocked and with it the hold of the cannula support, the adjusting element exerts a pressing force in the axial direction towards the main part and the main part is pushed in the direction towards the injection site as a result. This causes additional pain stimulus to the body.

A safety needle arrangement of a design similar to that described in US 2007/0016148 A1 above is known from EP 0 830 871 B1 and parallel publication U.S. Pat. No. 5,928,199 A. However, this safety needle arrangement does not have an automatically operating adjusting element for returning the cannula to a position in which it is covered. When the locking device disposed between the main part and cannula support is released, the cannula support together with the cannula must be moved by the user manually in order to pull it back into the second position in which the cannula is covered.

The underlying objective of this invention is to propose a safety needle arrangement which can be automatically returned to a protected position once a locking device has been released, and the injection site or injection area of the body is not subjected to unnecessary additional pain stimulus as the safety needle arrangement is being removed and then taken away from the body.

This objective of the invention is achieved by features described herein. The advantages achieved as a result of the features reside in the fact that the first locking elements are formed by projections and are disposed in the region of the proximal end of the main part where they are also operated as a means of releasing the locking device. Accordingly, after use of the safety needle arrangement, it can be released by a simple one-handed operation and the used cannula then moved into the protected position. The engaged locking elements therefore have to be deliberately released by a user and the other movement into the protected position then takes place automatically due to the pretensioned adjusting element. Another advantage is the fact that the first locking elements are disposed diametrically opposite one another on the main part and can therefore be operated by the thumb and index finger of the user simultaneously for example, thereby obviating the need for a lateral withdrawing movement and hence a relative movement of the cannula inside the body. Due to this central releasing action followed by the automatic return of the cannula support together with the cannula into the protected position, no additional operating force is needed. The fact that the main part remains stationary relative to the body means that once the adjusting element has been released, no additional pressure is applied to the injection site. The cannula is simply moved into the protected position, namely into the covered position inside the main part, so that a safe position is obtained without any input on the part of the user, thereby preventing puncture injuries in the region of the used cannula.

Also of advantage is another embodiment with retaining arms connected in a flexible and resilient arrangement, because the retaining arms are capable of exerting a sufficiently strong spring force on the projections respectively disposed there to secure the cannula in the usage position with the co-operating locking elements in a securely latched position. This enables any unintentional release of the locking device to be prevented.

Also of advantage is an embodiment with projections projecting out in the radial direction because a releasing movement can be obtained from either side specifically directed in the direction towards the longitudinal axis. As a result, the mutually engaged first and second locking elements can be released simply by pushing the two retaining arms centrally together.

As a result of the embodiment with a holder piece that includes recesses constituting the second locking elements, the lock or latching of the mutually engaging first and second locking elements can be maintained until released accordingly by the user. Due to the fact that the projections respectively extend into recesses provided for this purpose, the locking device is prevented from being undesirably released.

Another embodiment in which the holder piece has oppositely-arranged insertion slots offers a possibility whereby the retaining arms together with the projections disposed thereon extending in the axial direction can be disposed inside the holder piece, thereby obtaining a protected locking area for the mutually engaging first and second locking elements.

Also of advantage is another embodiment in which the proximal end of the cannula support extends in the axial direction into the holder piece, and a housing orifice for the adjusting element is disposed in the holder piece extending across a partial length between the cannula support and the holder piece at the end remote from the main part, because a housing space can be obtained for the adjusting element in its pre-tensioned position. As a result, the adjusting element when in the usage position prior to a manipulation can be covered and kept reliably protected from outside. Accordingly, once the locking device has been released, the cannula support together with the cannula disposed thereon can always be automatically returned to the protected position inside the main part on an automated basis.

The advantage of the embodiment in which the cannula support is locked and retained on the main part via a locking device disposed in the region of the proximal end of the main part in its second position relative to the main part is that once the safety needle arrangement has been used, re-use of it again can be safely prevented. Not only does this enable undesired puncture injuries by the already used cannula to be prevented, but potential contamination or infection from the used cannula that could occur on re-use is also prevented.

As a result of the embodiment wherein wings are disposed on the main part extending out in the radial direction therefrom, the position of the safety needle arrangement as a whole during use for its intended purpose on the body can be more effectively fixed.

Finally, in another possible embodiment the wings extend out from the main part in the same direction as the projections disposed diametrically opposite one another on the retaining arms, which not only enables sufficient fixing on the body but also a releasing movement for the locking device that is oriented centrally and approximately parallel therewith.

Due to the embodiment defined in one of claim 11 or 12, a reduction in the speed of movement, namely the relative speed between the virtually to completely stationary main part and the cannula support, can be achieved. The purpose of the brake element or elements is to damp the rapid acceleration so as to create a slight restraining force at least at the start of the movement and the displacement force of the adjusting element must overcome this restraining force.

Another embodiment defined in claim 13 is of advantage. The high acceleration at the start of the displacement or displacement path is counteracted as a result.

However, the objective of the invention is also independently achieved by a method for taking a sample of fluid, in particular blood, from a body or for administering fluid to the body. The advantages obtained as a result of the combination of features reside in the fact that the first locking elements provided in the form of projections are disposed in the region of the proximal end of the main part where they are also operated as a means of releasing the locking device. Accordingly, after use, the safety needle arrangement can be released by a simple one-handed operation and the used cannula then moved into the protected position. The engaged locking elements therefore have to be deliberately released by a user and the other movement into the protected position then takes place automatically due to the pre-tensioned adjusting element. Another advantage is the fact that the first locking elements are disposed diametrically opposite one another on the main part and can therefore be operated by the thumb and index finger of the user simultaneously for example, thereby obviating the need for a lateral withdrawing movement and hence a relative movement of the cannula inside the body. Due to this central releasing action followed by the automatic return of the cannula support together with the cannula into the protected position, no additional operating force is needed. The fact that the main part remains stationary relative to the body means that once the adjusting element has been released, no additional pressure is applied to the injection site. The fact that the main part remains stationary relative to the body means that once the adjusting element has been released, no additional pressure is applied to the injection site. The cannula is simply moved into the protected position, namely into the covered position inside the main part, so that a safe position is obtained without any input on the part of the user, thereby preventing puncture injuries in the region of the used cannula.

To provide a clearer understanding, the invention will be described in more detail with reference to the appended drawings.

These are highly simplified, schematic drawings illustrating the following.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described.

Figure 1:
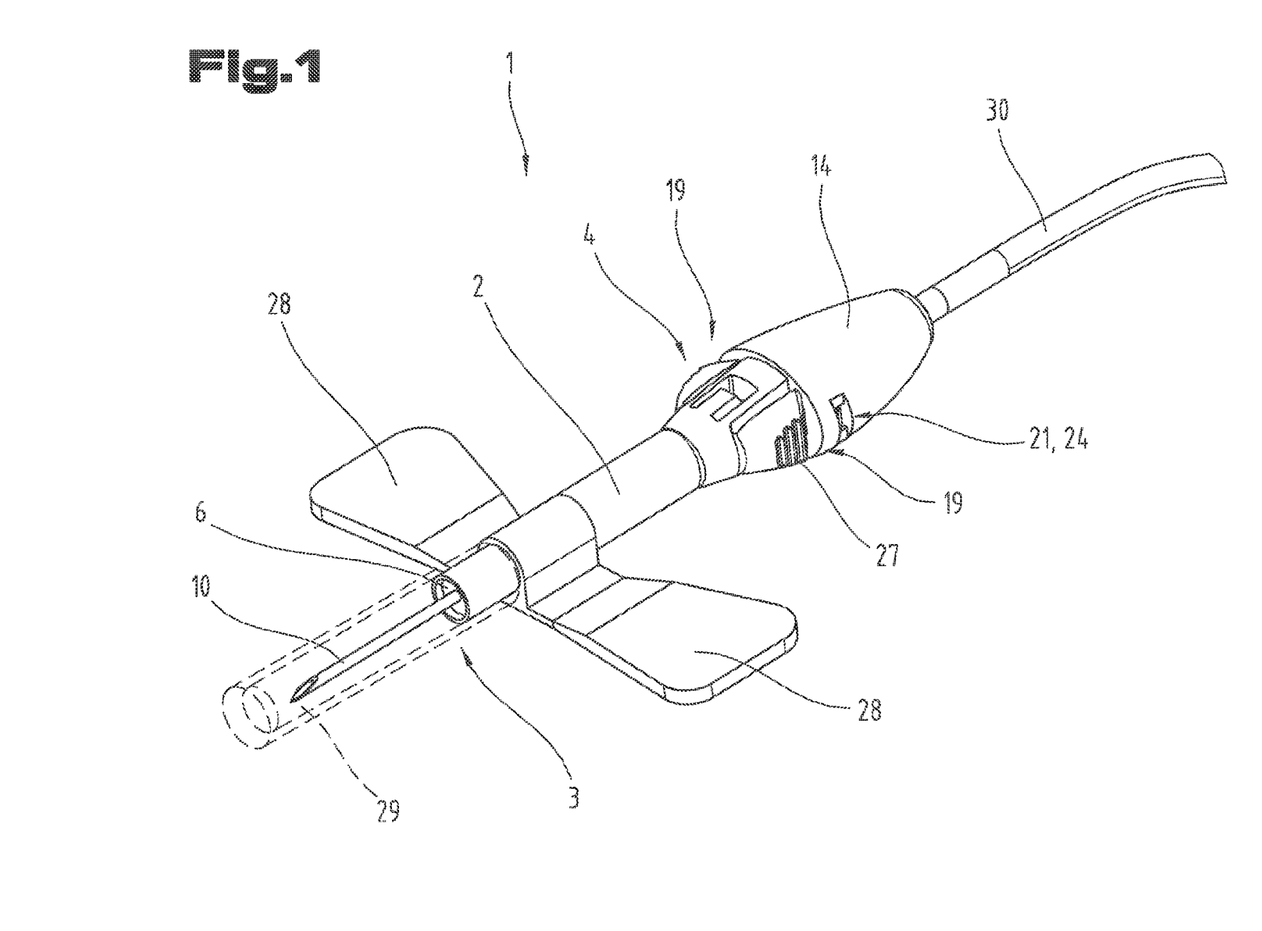
FIG. 1 a perspective diagram of a safety needle arrangement in its usage position.
Figure 2:
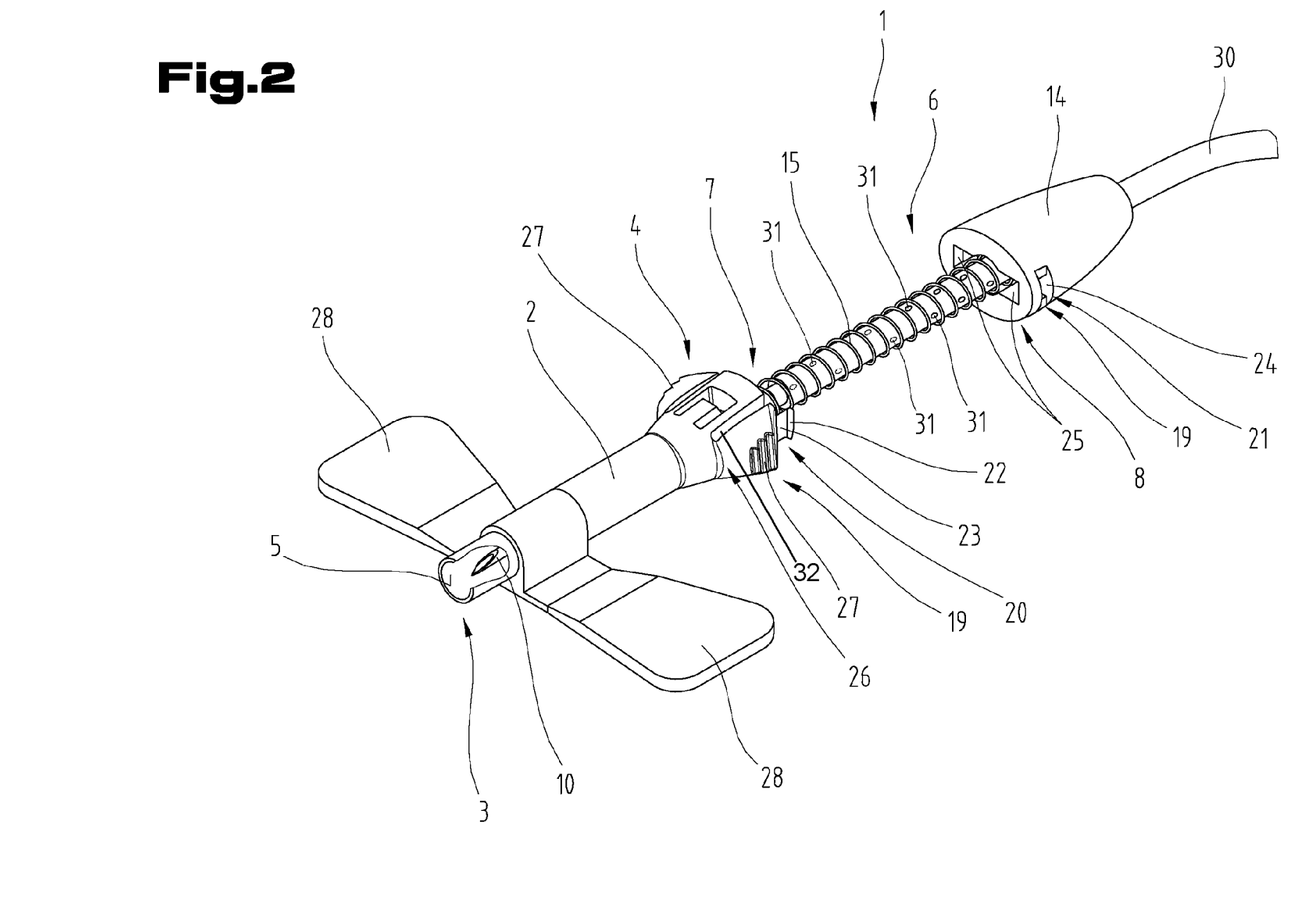
FIG. 2 a diagram in partial section illustrating the safety needle arrangement from FIG. 1 but with the cannula in its protected position.

FIGS. 1 to 4 illustrate a safety needle arrangement 1 which is used in the medical field. The safety needle arrangement 1 may be used for taking a sample of fluid, in particular blood, from a body or for administering fluid to the body, for example. A safety needle arrangement 1 based on such a design may also be referred to as a so-called "butterfly". FIGS. 1 and 2 illustrate the safety needle arrangement 1 in its assembled state but with the individual components in different positions.

Figure 3:
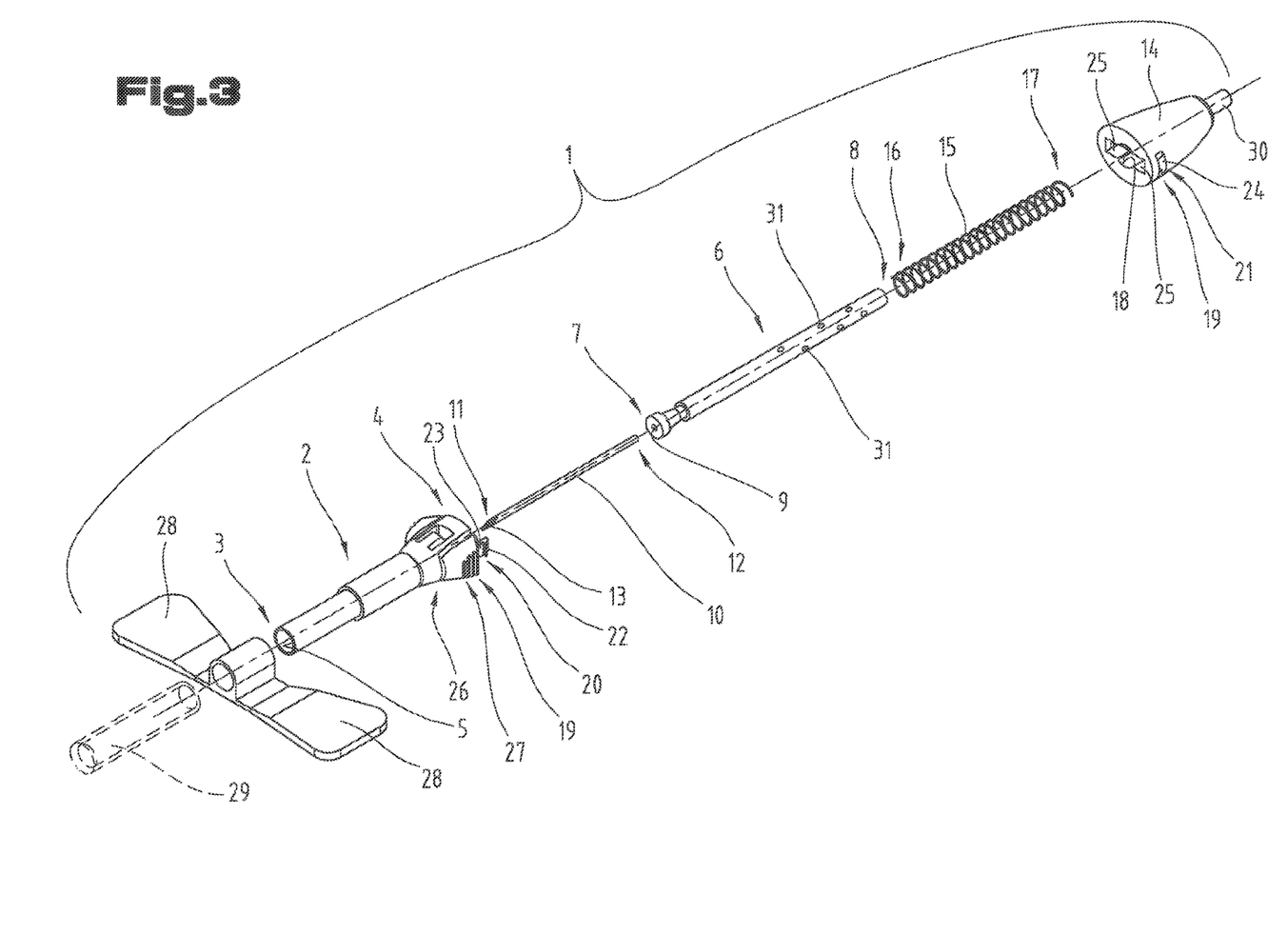
FIG. 3 an exploded diagram of the safety needle arrangement from FIGS. 1 and 2 with the individual components shown separately from one another.

FIG. 3 shows the individual parts and components of the safety needle arrangement 1 taken apart from one another in order to illustrate their design more clearly. Accordingly, the safety needle arrangement 1 may comprise a main part 2 with a distal end 3 and a proximal end 4. The main part 2 is preferably of a tubular, in particular cylindrical, shape and has an orifice 5 extending in the direction of its axial extension between the distal end 3 of the main part 2 and the proximal end 4 of the main part 2.

The safety needle arrangement 1 may also comprise a cannula support 6 which in turn has a distal end 7 and a proximal end 8 disposed at a distance apart therefrom in the axial direction. A flow orifice 9 extends through the cannula support 6 between the distal end 7 and the proximal end 8. The cannula support 6 is also designed so that it can be housed in the orifice 5 of the main part 2 and displaced in the axial direction, in particular guided.

The safety needle arrangement 1 may also comprise a cannula 10 which in turn has a distal end 11 and a proximal end 12 spaced apart therefrom in the axial direction. Extending inside the cannula 10 between the distal end 11 and the proximal end 12 is a flow passage 13. The proximal end 12 of the cannula 10 can be retained on the distal end 7 of the cannula support 6, in particular attached thereto, in a stationary arrangement. The proximal end 12 of the cannula 10 may be connected to the cannula support 6 by means of an at least airtight bonded connection. However, instead of or in addition to the bonded connection, it would also be possible to opt for a press fitting arrangement. To this end, the end regions of the cannula 10 and mounting orifice in the cannula support 6 are of correspondingly different dimensions.

Accordingly, fluid is able to flow from the distal end 11 of the cannula 10 through the flow passage 13 and on through the flow orifice 9 in the cannula support 6 or also in the opposite direction.

Furthermore, the cannula support 6 may also have an additional holder piece 14 in the region of its proximal end 8. The holder piece 14 may be provided either as a separate component or may be an integral part of the cannula support 6. If, as is the case in this example of an embodiment, separate components are provided, the proximal end 8 of the cannula support 6 extends into the holder piece 14 as viewed in the axial direction and is connected to it there. Here too, the mutual attachment or connection between the proximal end 8 of the cannula support 6 and the holder piece 14 may be provided in the form of an at least airtight bonded connection, for example. Independently thereof, however, instead of the bonded connection or in addition to it, it would also be possible to provide a press fitting arrangement. To this end, the end regions of the cannula support 6 and holder piece 14 are of correspondingly different dimensions.

To enable the cannula support 6 to be automatically displaced relative to the main part 2, the safety needle arrangement 1 may also comprise a separate adjusting element 15 which is disposed so as to act between the main part 2 and the cannula support 6 in the assembled state. In the embodiment illustrated as an example here, the adjusting element 15 is provided in the form of a helical compression spring extending around the external face of the cannula support 6. An adjusting element distal end 16 facing the main part 2 is supported on the proximal end 4 of the main part 2. The adjusting element 15 may also extend into the main part 2 across a partial length in the axial direction.

In the embodiment illustrated as an example here, the other proximal adjusting element end 17 spaced apart therefrom in the axial direction is supported on the holder piece 14. To ensure that there is sufficient space for the adjusting element 15 when the latter is in the compressed usage position or pre-tensioned position, it may be of advantage if the adjusting element 15 is able to extend into the holder piece 14 across a partial length at the end facing the main part 2. To this end, a housing orifice 18 for accommodating the adjusting element 15 is provided in the holder piece 14 at its end facing the main part 2, extending across a partial length between the cannula support 6 and holder piece 14. The cross-sectional shape of the housing orifice 18 is adapted to the dimensions of the adjusting element 15. In the embodiment illustrated as an example here, the housing orifice 18 is of a tubular or hollow cylindrical shape, for example.

FIG. 1 illustrates the first relative position of the cannula support 6 together with the cannula 10 attached to it. In this first position, the cannula 10 projects out from the distal end 3 of the main part 2.

FIG. 2 illustrates the so-called protected position which will be referred to here as the second position. In this second position, at least the distal end 11 of the cannula 10 is covered by the main part 2, thereby preventing puncture injuries by the used cannula. The cannula support 6 together with the cannula 10 attached to it is displaced, in particular axially displaced, automatically by the adjusting element 15 described above.

To enable the cannula support 6 together with the cannula 10 attached to it to be latched or locked in the first position relative to the main part 2, a separate locking device 19 is provided, which may also be an integral part of the safety needle arrangement 1. In this example of an embodiment, the locking device 19 comprises a number of first locking elements 20 and a number of second locking elements 21. When the locking device 19 is in the locking position, the first relative position of the cannula support 6 together with the cannula 10 relative to the main part 2 is fixed due to the mutually engaging first and second locking elements 20, 21.

In the embodiment illustrated as an example here, the first locking elements 20 are provided in the form of projections 22 disposed diametrically opposite one another and are disposed or arranged in the region of the proximal end 4 of the main part 2 and on the latter. The projections 22 may also be disposed respectively on a retaining arm 23 that is displaceable in the radial direction.

In the embodiment illustrated as an example here, the second locking elements 21 are provided in the form of recesses 24, likewise disposed diametrically opposite one another to enable the first locking elements 20 of the locking device 19 described above to latch. The second locking elements 21 are disposed in the region of the proximal end 8 of the cannula support 6. In the embodiment illustrated as an example here, the recesses 24 constituting the second locking elements 21 are disposed or arranged in the holder piece 14.

In order to accommodate the retaining arms 23 when the cannula support 6 is in the first position, the holder piece 14 may have insertion slots 25 disposed diametrically opposite one another in the region of its distal end facing the main part 2. Accordingly, the retaining arms 23 are able to extend into these insertion slots 25 when the cannula support 6 is in the first position and the projections 22 are in a latching or locking engagement with the recesses 24.

To enable the first locking elements 20—in this example of an embodiment projections 22—to move in the radial direction relative to the longitudinal extension of the main part 2, the retaining arms 23 may respectively be connected to the main part 2 in a flexible, in particular resilient, arrangement on linking sections 26 at the end remote from the projections 22 disposed thereon. The projections 22 may be disposed or arranged on the retaining arms 23 in such a way that they respectively project out from the retaining arms 23 in the radial direction towards the end remote from the orifice 5 disposed in the main part 2. Furthermore, the retaining arms 23, in terms of their axial extension between their linking sections 26 and projections 22, may be disposed respectively spaced apart from the main part 2. This spacing of the retaining arms 23 from the main part 2 can be achieved due to the provision or arrangement of slots 32 which terminate respectively in the region of the linking sections 26.

To enable better actuation of the retaining arms 23, an additional actuating means 27 may be disposed or arranged on the retaining arms 23 respectively between their linking sections 26 and projections 22. This makes it easier for the retaining arms 23 to be actuated in the radial direction towards the longitudinal axis. If, as is the case with the example of an embodiment described here, the retaining arms 23 with the actuating means 27 optionally provided or arranged thereon are disposed diametrically opposite one another, the locking device 19 can be more easily prevented from being inadvertently released. To obtain a release, it is necessary to deliberately move the two retaining arms 23 into the releasing position. The releasing action preferably takes place virtually simultaneously.

To prevent the locking device 19 from being accidentally released, an external dimension of the holder piece 14 in the region of its end facing the main part 2 may approximately correspond to the external dimension of the actuating means 27. This prevents the actuating means 27 from extending out beyond the holder piece 14.

Due to this radial displacement or movement of the projections 22, the latter move out of engagement with the recesses 24, thereby releasing the locking device 19. As soon as the locking device 19 is released, the adjusting element 15 comes into action and automatically moves the cannula support 6 and hence also the cannula 10 into its covered position.

To prevent the safety needle arrangement 1 from being used again, the cannula support 6 can be locked and maintained in its second position relative to the main part 2 by means of a locking device disposed in the region of the proximal end 4 of the main part 2 to prevent any movement in the axial direction relative to the main part. This locking device may be designed so that when the cannula support 6 is disposed in the second position, it is prevented from moving again in both directions as viewed in the axial direction. This makes it impossible to detach the cannula support 6 from the main part 2 and at the same time also prevents the cannula support 6 from being returned to the first position.

Furthermore, wings 28 may be provided or disposed on the main part 2 extending out therefrom in the radial direction. Disposed in a mutually abutting position, the purpose of the wings 28 is to give the user a better hold during the injection process. Once the safety needle arrangement 1 with its cannula 10 has been inserted for taking a fluid sample from the body or for administering fluids to the body, the entire safety needle arrangement 1 can be held or secured on the surface of the body, not illustrated, by the wings 28 using an additional adhesive tape or some other retaining means.

Furthermore, the wings 28 may respectively extend out from the main part 2 in the same direction as the projections 22 disposed diametrically opposite one another on the retaining arms 23. This enables a clear orientation of the first locking elements 20 relative to the surface, i.e. body skin, to be obtained.

Being strongly pre-tensioned at the start of the movement, the adjusting element 15 initiates the movement with full force and hence a high acceleration and the rapid automatic movement can lead to body fluid, in particular drops of blood, being spattered. This causes a high risk of infection.

Figure 4:
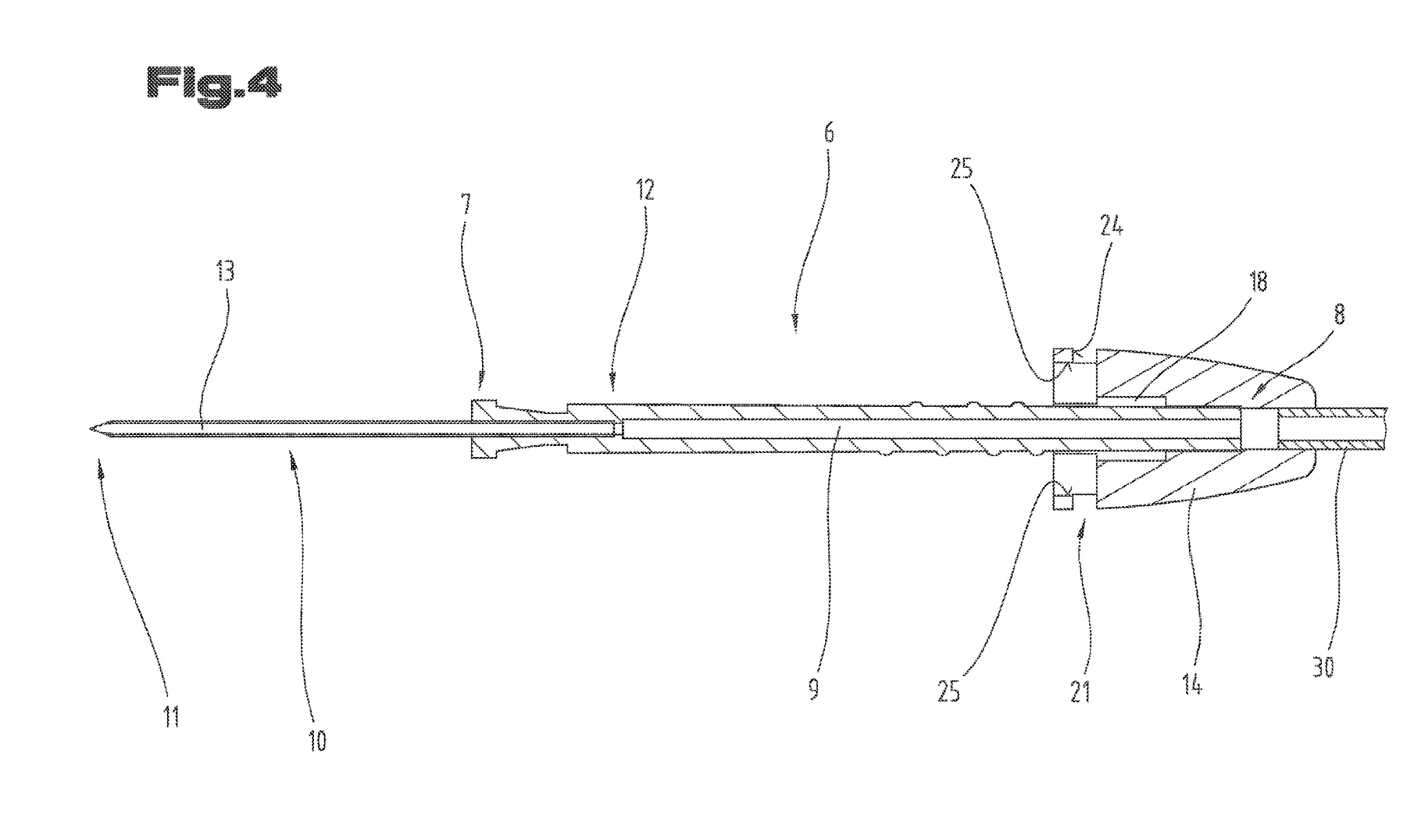
FIG. 4 an axial section of the cannula support with the cannula and holder piece.

In order to reduce the speed of movement, namely the relative speed between the virtually to completely stationary main part 2 and the cannula support 6, at least one brake element 31 in the form of a projection or shoulder is provided or disposed in the surface of the preferably tubular cannula support 6, as illustrated on a very simplified basis in FIGS. 2 to 4. The purpose of the brake element or elements 31 is to damp the rapid acceleration. This braking or damping effect can also be achieved by increasing the friction between the main part 2 and the cannula support 6. The braking or damping effect can be set depending on the design, disposition and/or number of brake elements 31.

In the embodiment illustrated as an example here, only a few brake elements 31 are provided or disposed in the region of the proximal end 8 of the cannula support 6, as schematically illustrated. These counteract the high acceleration at the start of the movement or displacement path. The brake elements 31, which preferably project out from the cannula support 6, co-operate with the orifice 5 in the main part 2 so as to create a slight restraining force at least at the start of the movement and the displacement force of the adjusting element 15 must overcome this restraining force.

However, it would also be possible to provide or dispose the brake elements 31 not just for the start of the movement of the cannula support 6 but to provide them for the entire axial length, as illustrated by broken lines in FIG. 2. This enables the number and/or height, i.e. the degree to which they extend out from the cannula support 6, to be influenced. For example, by opting for a lesser number and/or a smaller extension of the brake elements 31 than those brake elements 31 influencing the start of the movement, the braking effect during the movement can be reduced.

A fluid sample, in particular blood, can be taken from the body or a fluid administered to the body by means of the safety needle arrangement 1 described above by implementing the steps described below. To this end, a tube 30 can be fitted or attached to the proximal end 8 of the cannula support 6 and/or holder piece 14 by its first end. The various connectors or devices can be attached to and thus coupled with the other end, although this is not illustrated.

In this respect, it should be noted that it is not absolutely necessary to keep to this sequence and the individual steps can also be implemented in a different sequence.

In the non-assembled state, the safety needle arrangement 1 is usually packaged in a sterile packaging and the user has to remove it first of all. The cannula support 6 together with the cannula 10 retained on it is in the first position in which the cannula 10 extends beyond the distal end 3 of the main part 2. In order to prevent needlestick injuries in this state, an additional, preferably tubular, guard 29 is provided, as indicated by broken lines in FIG. 1. The guard 29 can only be provided in the form of a tubular component open at both ends and the entire safety needle arrangement 1 is then packaged in an additional sterile main pack, e.g. a blister pack, not illustrated, until needed for its intended use.

The guard 29 may also be closed in a sealed arrangement in the region of its distal end remote from the main part 2, as illustrated by the guard 29 shown in broken lines. This may be in the form of a terminating wall, for example. This design of guard 29 might also be described as a protective cap. This enables at least the cannula 10 to be kept sterile before being used for its intended purpose, in which case a standard main pack that would usually otherwise be used, such as a bacteria-proof blister pack, can be dispensed with altogether. This saves on packaging material whilst nevertheless ensuring that the cannula 10 remains sterile until it is used.

After removing this guard 29 or protective cap from the main part 2, the cannula 10 is free and can then be placed on the intended injection site in readiness for injecting the body.

A check can then be made to ensure that the cannula 10 is in the correct position on the body. In another step, a sample of fluid, in particular blood, can be taken from the body. Irrespective of this, it would also be possible to introduce fluid into the body by means of the safety needle arrangement 1.

The cannula 10 is removed from the injection site of the body by holding the main part 2 of the safety needle arrangement 1 stationary relative to the body. The engaged locking device 19 between the main part 2 and the cannula support 6 is then disengaged. This is done by simultaneously moving the projections 22 of the locking device 19 disposed diametrically opposite one another on the main part in the direction towards the longitudinal axis of the main part 2. As this happens, the projections 22 are disengaged from the recesses 24 disposed in the cannula support 6, in particular its holder piece 14. After releasing the locking device 19, the cannula support 6 together with the cannula 10 retained on it is automatically moved into the second position by means of the adjusting element 15. As a result, the cannula 10 can be automatically pulled away from the injection site and is then moved into the second relative position described above. In this second position, at least the distal end 11 of the cannula 10 is covered by the main part 2. During this automatic retraction, which merely has to be triggered by the user, the main part 2 may remain on the body unchanged in terms of its position. This avoids any unnecessary relative movements of the safety needle arrangement 1 whilst the cannula 10 is still in the injection site.

Once the protected position has been reached, the entire safety needle arrangement 1 can be taken away or removed from the body. The used safety needle arrangement 1 is then disposed of in accordance with safety regulations and steps taken to ensure it is kept safe accordingly until finally disposed of.

The embodiments illustrated as examples represent possible variants of the safety needle arrangement 1 and it should be pointed out at this stage that the invention is not specifically limited to the variants specifically illustrated, and instead the individual variants may be used in different combinations with one another and these possible variations lie within the reach of the person skilled in this technical field given the disclosed technical teaching.

Furthermore, individual features or combinations of features from the different embodiments illustrated and described may be construed as independent inventive solutions or solutions proposed by the invention in their own right.

The objective underlying the independent inventive solutions may be found in the description.

For the sake of good order, finally, it should be pointed out that, in order to provide a clearer understanding of the structure of the safety needle arrangement 1, it and its constituent parts are illustrated to a certain extent out of scale and/or on an enlarged scale and/or on a reduced scale.

| List of reference numbers | |
|---|---|
| 1 | Safety needle arrangement |
| 2 | Main part |
| 3 | Distal end |
| 4 | Proximal end |
| 5 | Orifice |
| 6 | Cannula support |
| 7 | Distal end |
| 8 | Proximal end |
| 9 | Flow orifice |
| 10 | Cannula |
| 11 | Distal end |
| 12 | Proximal end |
| 13 | Flow passage |
| 14 | Holder piece |
| 15 | Adjusting element |
| 16 | Adjusting element distal end |
| 17 | Adjusting element proximal end |
| 18 | Housing orifice |
| 19 | Locking device |
| 20 | First locking element |
| 21 | Second locking element |
| 22 | Projection |
| 23 | Retaining arm |
| 24 | Recess |
| 25 | Insertion slot |
| 26 | Linking section |

| List of reference numbers | |
|---|---|
| 27 | Actuation means |
| 28 | Wing |
| 29 | Guard |
| 30 | Tube |
| 31 | Brake element |
| 32 | Slot |

The invention claimed is:

1. A safety needle arrangement comprising:

a main part having a distal end and a proximal end, an orifice extending therethrough between the distal end of the main part and the proximal end of the main part, a cannula support having a distal end and a proximal end, a flow orifice extending between the distal end of the cannula support and the proximal end of the cannula support, and the cannula support is accommodated in the orifice of the main part so as to be displaceable in an axial direction, a cannula having a distal end and a proximal end, a flow passage extending inside the cannula between the distal end of the cannula and the proximal end of the cannula, the proximal end of the cannula being retained on the distal end of the cannula support, an adjusting element which is operatively arranged between the main part and the cannula support, wherein the adjusting element automatically moves the cannula support together with the cannula retained thereon from a first position, in which first position the cannula projects beyond the distal end of the main part, into a second position, in which second position at least the distal end of the cannula is covered by the main part, a first locking device having multiple first and second locking elements, the first locking device configured to lock the cannula support together with the cannula in the first position relative to the main part when the first and second locking elements are in a mutually engaging position, and the first locking elements are disposed in a main part region of the proximal end of the main part, wherein the first locking elements are formed by at least a first projection and a second projection disposed diametrically opposite one another, wherein the first projection is disposed on a first retaining arm that is displaceable in a radial direction and the second projection is disposed on a second retaining arm that is displaceable in the radial direction, a holder piece provided or disposed on the cannula support in a region of the proximal end of the cannula support, the holder piece having a first insertion slot and a second insertion slot, the second insertion slot being disposed diametrically opposite to the first insertion slot, and a tubular guard arranged on the distal end of the main part, wherein the first retaining arm and the second retaining arm are connected to the main part in a flexible and resilient arrangement, wherein the first retaining arm is connected on a first linking section at a first end remote from the first projection disposed thereon, and wherein the second retaining arm is connected on a second linking section at a second end remote from the second projection disposed thereon, wherein the first retaining arm is spaced apart from the main part between the first linking section and the first projection under provision or arrangement of a first slot terminated in a first linking section region of the first linking section, wherein the second retaining arm is spaced apart from the main part between the second linking section and the second projection under provision or arrangement of a second slot terminated in a linking section region of the second linking section, wherein the second locking elements are formed by recesses disposed diametrically opposite one another, the recesses being disposed in said holder piece, wherein the first insertion slot and the second insertion slot of the holder piece are disposed facing the distal end of the cannula support, wherein the first retaining arm extends into the first insertion slot when the cannula support is disposed in the first position, wherein the second retaining arm extends into the second insertion slot when the cannula support is disposed in the first position, and wherein the tubular guard prevents needlestick injuries from the cannula in the first position.

2. The safety needle arrangement according to claim 1, wherein the first projection projects out from the first retaining arm in the radial direction, and the second projection projects out from the second retaining arm in the radial direction, wherein the first retaining arm has an axial first extension between the first linking section and the first projection, wherein the second retaining arm has an axial second extension between the second linking section and the second projection, and wherein the first retaining arm and the second retaining arm are disposed respectively spaced apart from the main part.

3. The safety needle arrangement according to claim 1, wherein the proximal end of the cannula support extends in the axial direction into the holder piece, and wherein a housing orifice for the adjusting element is disposed in the holder piece extending across a partial length between the cannula support and the holder piece.

4. The safety needle arrangement according to claim 1, wherein the cannula support is locked and retained on the main part via a second locking device disposed in the main part region of the proximal end of the main part in its second position relative to the main part.

5. The safety needle arrangement according to claim 1, wherein wings are disposed on the main part extending out in the radial direction therefrom.

6. The safety needle arrangement according to claim 5, wherein the first projection projects from the main part in a first direction, wherein the second projection projects out from the main part in a second direction, wherein a first wing of the wings extends out from the main part in the first direction, and wherein a second wing of the wings extends out from the main part in the second direction.

7. The safety needle arrangement according to claim 1, further comprising a first brake element in the form of a projection or shoulder disposed or arranged on a surface of the cannula support.

8. The safety needle arrangement according to claim 7, further comprising a second brake element, wherein the first brake element and the second brake element project out from the cannula support through the orifice disposed in the main part in order to reduce a speed of movement between the main part and the cannula support displaceable relative thereto via the adjusting element from the first position into the second position.

9. The safety needle arrangement according to claim 7, wherein the first brake element is disposed or arranged at least in the region of the proximal end of the cannula support.

10. The safety needle arrangement according to claim 7, further comprising a plurality of brake elements which may include the first brake element, wherein the plurality of brake elements is provided across an entire axial length of the cannula support.

* * * * *